United States Patent [19]

Hall

[11] 4,178,919
[45] Dec. 18, 1979

[54] FLOWMETER FOR PROVIDING SYNCHRONIZED FLOW DATA AND RESPIRATORY GAS SAMPLES TO A MEDICAL MASS SPECTROMETER

[75] Inventor: Lawrence G. Hall, Creve Coeur, Mo.

[73] Assignee: The Perkin-Elmer Corporation, Norwalk, Conn.

[21] Appl. No.: 893,033

[22] Filed: Apr. 3, 1978

[51] Int. Cl.² ............................................. A61B 5/08
[52] U.S. Cl. .................................. 128/719; 128/725; 23/232 E; 73/421.5 R; 250/294; 422/84
[58] Field of Search ..................... 128/2.07, 2.08, 2 C; 73/421.5 R; 23/232 R, 232 E; 422/83, 84; 250/294

[56] References Cited

U.S. PATENT DOCUMENTS 3,824,390  7/1974  Magyar ................................ 250/294
3,896,792  7/1975  Vail et al. ............................ 128/2.07

OTHER PUBLICATIONS

Green et al, "A Simplified Closing Volume Method . . ." The Lancet, Oct. 28, 1972, pp. 905-906.

Primary Examiner—Lee S. Cohen
Attorney, Agent, or Firm—Salvatore A. Giarratana; Francis L. Masselle; Edwin T. Grimes

[57] ABSTRACT

Respiratory gas flow data is synchronously provided along with continuous samples of the gases for analysis by a medical mass spectrometer. The gas flow data is determined by use of the differential pressure across a resistive core in a sampling flowmeter and the flow value at any instant is registered by proportionately admitting a non-toxic gas that is foreign to the normal respiratory gases into the sampling inlet in a quantity controlled by the differential pressure. The quantity of foreign gas therefore represents flow and is drawn through the inlet tube in exact synchronism with its corresponding respiratory gas sample for analysis by the spectrometer. The generated signal representing the amount of foreign gas, hence the flow, may then be used with the signals representing concentration of the various gases in the corresponding respiratory gas sample to calculate various medical parameters, such as oxygen uptake, where the exact synchronism of these signals is important.

6 Claims, 1 Drawing Figure

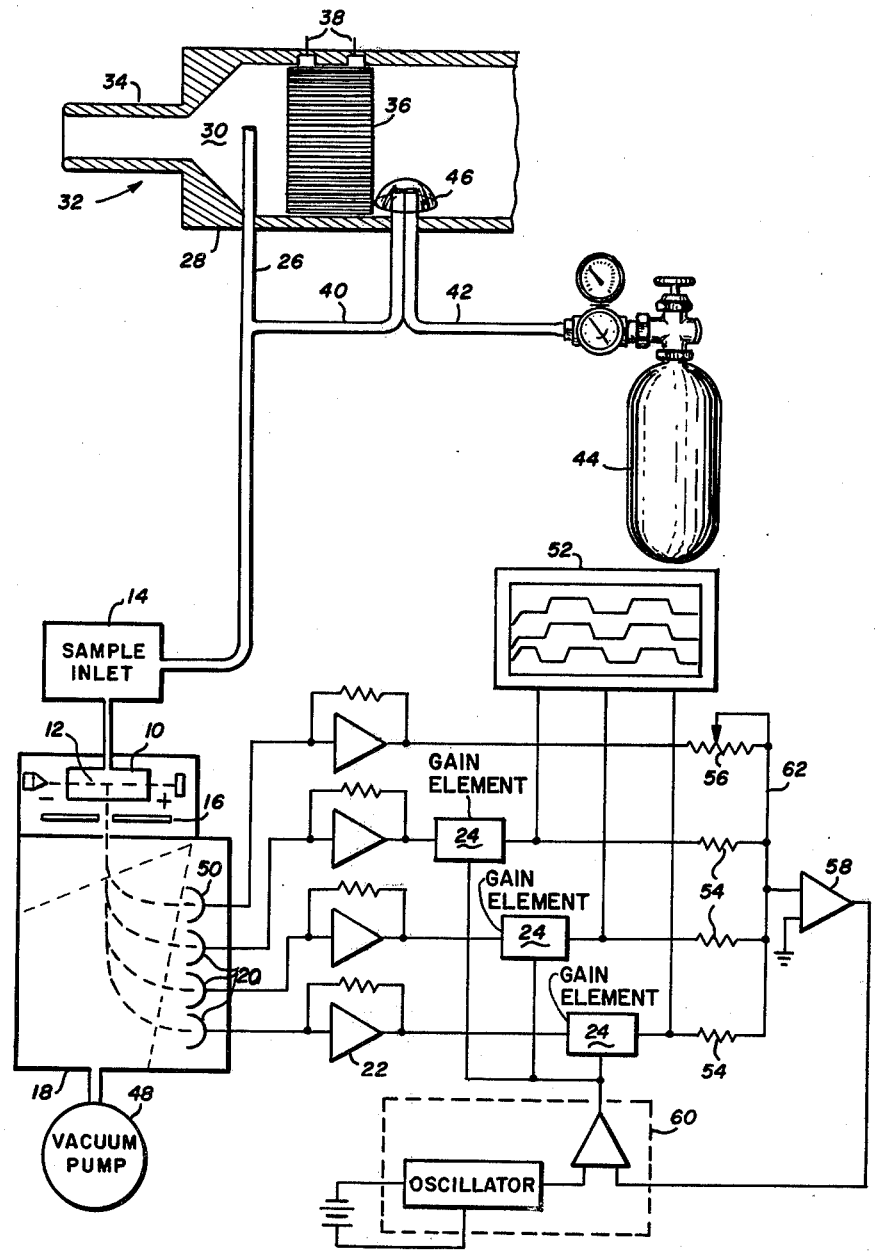

FLOWMETER FOR PROVIDING SYNCHRONIZED FLOW DATA AND RESPIRATORY GAS SAMPLES TO A MEDICAL MASS SPECTROMETER

This invention relates generally to medical gas analysis and more particularly to the determination of the percentage of each gas in the rapidly changing composition of respiratory gases.

Respiratory gases are readily analyzed by the use of a medical mass spectrometer which continuously receives small samples of the combined gases, reduces the pressure through a molecular leak so that the combined gas molecules may be ionized by electron bombardment, and then subjects the ionized gas molecules to a magnetic field that segregates various gas molecules according to their respective mass to charge ratios. Ion current collector cups are positioned to receive the ions of the particular gases of interest in the mixture and produce currents proportional to the quantity of that gas admitted to the system.

The output of the spectrometer is coupled to circuitry that includes electrometers that receive the ion currents and which are individually calibrated so that the ions of each gas will appear equally sensitive to the system and so that equal quantities of each type of gas will be represented as electrometer output voltage signals of equal amplitudes. Each electrometer output signal is applied to the variable gain control element, each of which is individually adjusted by an identical factor, derived from the sum of all electrometer output signals, to form a closed loop gain control in which the sum of all electrometer output signals is a constant value regardless of uncontrolled gain changes that may appear in the system. The output voltage from each gain element then represents a precise percentage of its corresponding gas in the combined gas sampled by the respiratory gas flowmeter.

Where it is desired to compute various medical parameters, such as oxygen uptake of a patient, it is necessary to measure respiratory gas flow in synchronized time with the respiratory gas composition so that the product of these two variables will accurately represent the instantaneous value of partial flow of each gas component. In one prior art system, the flow data was obtained by a differential pressure sensor coupled across the resistive core of the flowmeter and the signal generated thereby was electronically delayed so that it would be synchronized with the arrival of the gas sample. But gas flow through a capillary tube is seldom constant, even under the best working conditions and varies with gases of different viscosity, temperature, and water content, which itself may vary so greatly that it may partially block the capillary tube when respiratory gas samples are being taken from an intensive care patient. In the present invention, gas flow data continuously flows through the capillary conduit between the sampling flowmeter and the spectrometer along with the associated respiratory gas samples. Thus, the prior art deficiencies are overcome irrespective of changes or variations in the transit time of the gas samples between the respiratory flowmeter and the medical mass spectrometer.

Briefly described, the invention is for a system in which a gas flowmeter with a restricting core is provided with a respiratory gas sampling tube on the proximal or mouthpiece side of the core and a second input tube on the outboard or distal side of the core, both sampling tubes being coupled together and to the input port of a medical mass spectrometer. The distal sampling tube is paired with a tube that emits a gas such as helium, that is foreign to the respiratory system and both tubes may be very loosely capped so that the distal sampling tube receives the foreign gas only, and at the pressure existing at the distal side of the core. When there is no inspiration or expiration through the flowmeter and the pressures at both proximal and distal sides of the core are equal, the vacuum system of the mass spectrometer draws a representative sample of the respiratory gases from the proximal sampling tube and a small sample of the foreign gas through the distal tube. The electrometer output voltage signals in the mass spectrometer may then be properly calibrated for the nominal quantity of the foreign gas. During respiratory inspiration and expiration, the flow resistance of the flowmeter produces pressure differences across the core, thus drawing a greater or less flow of the foreign gas compared with the sample of respiratory gas. The varying amounts of the foreign gas are drawn into the system and are analyzed to provide a signal proportional to flow. Consequently, the generated signals representing flow and gas composition occur at identical times and can be used for computation of medical parameters whose validity depends upon the accurate synchronization of the two types of data.

DESCRIPTION OF THE DRAWINGS

In the drawing that illustrates a preferred embodiment of the invention:

The single FIGURE is a schematic block diagram illustrating the arrangement of a respiratory flowmeter connected to a typical medical mass spectrometer.

DETAILED DESCRIPTION

Illustrated in the drawing is a typical medical mass spectrometer, such as that taught by the Magyar U.S. Pat., No. 3,824,390, which includes an evacuated ionization chamber 10 through which an electron beam 12 is passed to ionize gas molecules that are admitted to the chamber 10 from a sample inlet 14 such as a conventional molecular leak which, without disturbing the composition of a gas sample, reduces its pressure to a level compatible with the degree of vacuum provided in the chamber 10. The gas samples thus ionized are focused by electrode 16 and accelerated into an analyzing chamber 18 where the ionized gas molecules are subjected to a magnetic field that deflects the course of the ions into curved paths according to the respective mass to charge ratios of the various gas molecules therein. Collector cups 20, appropriately positioned with the analyzing chamber 18 to receive the deflected ions of each of the gases of interest, produce currents proportional to the quantity of gas ions collected.

The spectrometer is coupled to circuitry containing electrometers 22 that receive the ion currents and generate voltage signals representing the magnitude of those currents. As described in the aforementioned Magyar U.S. Pat. No. 3,824,390, the voltage signals are then applied to voltage controlled gain amplifiers 24 that are calibrated, as previously described, to produce output signals that are summed together with a reference voltage produced by a pressure transducer that generates a reference voltage proportional to the pressure of the gases in the gas transmission tube 26 to generate a control voltage for controlling the gain elements 24.

In the present invention, the pressure signals representing respiratory gas flow, are obtained by measuring the amount of foreign gas drawn into the inlet by the pressure differential across the resistive core in the flowmeter. Since the foreign gas passes into the spectrometer along with its corresponding gas sample, both the gas sample and the flow data are always synchronized, irrespective of the transit time between the sampling flowmeter and the spectrometer.

As illustrated in the FIGURE, the gas transmission tube 26, which is preferably a very small capillary tube, is introduced through the wall 28 and into the sampling area 30 in the air stream of a respiratory flowmeter 32. The flowmeter illustrated in the drawing is a Fleisch type of pneumotachograph flowmeter section of a pulmonary head assembly having a mouthpiece 34 at the proximal end of a hollow body containing a laminar flow core 36. Core 36 is preferably comprised of a section of corrugated metal foil suitably arranged to induce a laminar airflow of gases by the pressure ports 38 which are normally connected to a pressure transducer but which are not utilized in the present invention.

Connected through the wall 28 and into flowmeter 32 and distal of the core 36 is a capillary tube which will be referred to as the difference tube 40. A gas supply tube 42 which is connected to a source 44 of a gas, such as helium that is foreign to the respiratory gases, is coupled with difference tube 40 to terminate within a gas collector cup 46. Cup 46 may simply be an inverted plastic hemisphere that will trap the light foreign gas to assure that the difference tube 40 receives nothing but the foreign gas. Further, cup 46 should be open on the bottom to assure that the foreign gas taken by the difference tube 40 is at the pressure existing in the distal end of the sampling flowmeter.

In operation, the foreign gas from source 44 is admitted through the gas supply tube 42 at a rate of approximately 0.02 milliliters per second while there is no gas flow through the flowmeter 32 and the mouthpiece 34 is open so that there is no pressure difference across the flowmeter core 36. The vacuum pump 48 associated with the medical mass spectrometer draws atmospheric gases from the area 30 and also the foreign gas through the difference tube 40. It is essential that the foreign gas sample is drawn concurrently with the drawing of gas from area 30 and that the two samplings be mixed together so that the combined gases received at the spectrometer will contain the gas sample to be analyzed along with the gas representing the pressure of that gas sample. Therefore, the foreign gas sample from the cup 46 must reach the junction of the difference tube 40 and the gas transmission tubes 26 at the same time as the gas sample drawn from sampling area 30. This may be achieved by making the two tubes, between their ends and their junction, of equal lengths, or with appropriate lumen differences.

The gases thus synchronously combined are drawn by a vacuum pump (not shown) associated with the sample inlet 14, through the transmission tube and into the sample inlet 14 where a very small sample is admitted into the ionization chamber 10 in which the molecules of the various gases are ionized and accelerated into the analyzing chamber 18. The respiratory gas ions are then accelerated, deflected, and received by the appropriately positioned collector cups 20, while the foreign gas ions are received only in the properly positioned collector cup 50. The currents from cups 20 and 50 are each applied to the pre-calibrated electrometers 22 which convert the currents into corresponding standardized voltage levels as previously described. These signals, representing the ions received by the collector cups 20, are applied to voltage controlled gain elements 24, the output terminals of which are coupled to an appropriate display 52 that will indicate the percentage of each gas in a respiratory gas sample. The gain element output signals are also coupled through resistances 54 which form a summing circuit. The voltage level from the electrometer representing the current received by the foreign gas molecule cup 50 is applied through a variable resistor 56 to the summing circuit, the output of which is applied to the input terminal of a high gain summing amplifier 58. The output from amplifier 58 is coupled to a duty cycle modulator circuit 60 that generates, from the D.C. output of amplifier 58, square wave output voltage signals which vary in accordance with changes in the relationship between the reference voltage produced by the presence of the foreign gas received by collector cup 50 and the total of the voltages from the gain elements 24. This square wave voltage signal is then applied to each electrometer 24 to provide a closed loop gain control. The complete description of the duty cycle modulator 60 and the closed loop gain control circuitry is contained within the aforementioned Magyar U.S. Pat., No. 3,824,390.

During system calibration, the variable resistor 56 is adjusted so that the gas compositions displayed on the display 50 will total 100%. The calibrated gain elements will now correct for any uncontrolled gain changes of the system and the spectrometer system has now been properly adjusted and respiratory gases may be analyzed. When a patient inhales, the inspired gases are sampled in the sampling area 30 by the gas transmission tube 26. The gas flow through the core 36 lowers the pressure in the area 30 below that in the distal end so that the difference tube 40 will draw a larger quantity of the foreign gas supplied by the gas supply tube 42 into the collecting cup 46. Since the collecting cup 46 is preferably positioned near one wall of the flowmeter 32 while the inlet of the gas transmission tube 26 is positioned near the center of the airstream in area 30, any excess of the foreign gas that escapes from the cup 46 will be directed, by the laminar flow action of core 36, away from the inlet of the transmission tube 26 so that tube 26 will accurately sense only those gases in the area 30 while the amount of foreign gas conducted through the difference tube 40 is a direct indication of the pressure difference across the core 36, and hence the flow through the flowmeter.

When the patient exhales, the expired respiratory gases passing through the core 36 produce an increase in pressure in the sampling area 30 over that in the distal end, resulting in a proportional increase in pressure at the junction of the difference tube 40 with the transmission tube 26. This increase in pressure at the junction causes a reduction in the flow of the foreign gas into the system so that when the respiratory gas sample arrives at the mass spectrometer, the gas pressure information, in the form of a reduced quantity of foreign gas molecules, will be simultaneously received. The varying quantities of foreign gas received at the spectrometer will thereafter result in signals that will alter the reference voltage applied to the summing circuit through conductor 62 to correspondingly alter the control signal to the elements 24 so that they will generate accurate indications of the respiratory gas content in percent of each gas present at each instant during the sampling process.

What is claimed is:

1. A flowmeter for providing synchronized gas flow data concurrently with gas samples to a mass spectrometer comprising:
    a mass spectrometer having an input port,
    a tubular flowmeter element for a gas flow to be sampled and having a first end, a second end, and a flow restricting means interposed between said first and second ends;
    a gas transmission tube connecting the first end of said flowmeter element to said input port of said mass spectrometer;
    first means for introducing a second gas into the second end of said flowmeter element, said second gas being foreign to the gases to be sampled;
    conduit means coupled between said second end and said gas transmission tube, one end of said conduit means positioned in said second end to withdraw only said second gas, the other end of said conduit means being connected into said transmission tube at a point where a sample of gas will combine with said second gas withdrawn at substantially the same instant as said sample; and
    second means within said mass spectrometer for measuring the quantity of second gas in the combined sample transmitted to said mass spectrometer, said quantity being proportional to the pressure difference across said flow restricting means and indicative of the gas flow through said flowmeter.

2. The flowmeter claimed in claim 1 comprising a gas collector cup opened to said second end of said flowmeter element for receiving said second gas from said first means, and said one end of said conduit means opens into said cup to withdraw only said second gas at the pressure of said second end.

3. The flowmeter claimed in claim 2 wherein said second gas is helium and said gas collector cup is inverted to collect said helium.

4. The flowmeter claimed in claim 2 wherein said conduit means and said transmission tube are capillary tubes.

5. The flowmeter claimed in claim 4 comprising a patient's mouthpiece and wherein said flowmeter element is a pneumotachograph flowmeter in which said first end is coupled to said patient's mouthpiece.

6. A method for transmitting pressure data of a flowing gas simultaneously with samples of said gas comprising the steps of:
    providing a sampling element through which said gas flows, said element having a first end coupled to a pressure varying source of said gas, a second end, and a flow-restricting means within said element and interposed between said first and said second ends for creating a pressure difference between said first and second ends that is proportional to the gas flow through said restricting means;
    withdrawing samples of said gas with a sampling tube positioned within said first end of said element;
    admitting into the second end of said element a second gas that is distinguishable from said sampled gas;
    positioning a withdrawing tube within said second end and proximate the location where said second gas is admitted, withdrawing samples of only said second gas with said withdrawing tube and at the pressure existing in said second end;
    interconnecting said gas sampling tube and said second gas withdrawing tube at a location near said sampling element and at locations in said tubes where a sample of said sampled gas will arrive and combine with a sample of said second gas that was withdrawn from said sampling element at substantially the same instant; and
    determining the quantity of second gas in the combined sampled gas and second gas, said quantity being proportional to the pressure difference existing between said first and said second ends of said sampling element at the instant said sampled gas was withdrawn.

* * * * *